(12) United States Patent
Bergmann et al.

(10) Patent No.: US 10,228,316 B2
(45) Date of Patent: Mar. 12, 2019

(54) CONDENSATION PARTICLE COUNTER WITH SATURATION UNIT AND DOWNSTREAM CONDENSATION UNIT

(71) Applicant: AVL LIST GMBH, Graz (AT)

(72) Inventors: Alexander Bergmann, Graz (AT); Manuel Unger, Stainz (AT)

(73) Assignee: AVL LIST GMBH, Graz (AT)

( * ) Notice: Subject to any disclaimer, the term of this patent is extended or adjusted under 35 U.S.C. 154(b) by 656 days.

(21) Appl. No.: 14/811,239

(22) Filed: Jul. 28, 2015

(65) Prior Publication Data

US 2016/0033384 A1    Feb. 4, 2016

(30) Foreign Application Priority Data

Jul. 29, 2014    (AT) ............................... A 50538/2014

(51) Int. Cl.
*G01N 15/06* (2006.01)
*G01N 15/14* (2006.01)
*G01N 15/00* (2006.01)

(52) U.S. Cl.
CPC ....... *G01N 15/065* (2013.01); *G01N 15/1434* (2013.01); *G01N 2015/0046* (2013.01); *G01N 2015/1486* (2013.01)

(58) Field of Classification Search
CPC ............. G01N 15/065; G01N 15/1434; G01N 2015/1486; G01N 2015/0046
See application file for complete search history.

(56) References Cited

U.S. PATENT DOCUMENTS

| 3,738,751 | A |   | 6/1973  | Rich |              |
|-----------|---|---|---------|------|--------------|
| 4,790,650 | A | * | 12/1988 | Keady | ................. G01N 15/065 |
|           |   |   |         |       | 356/337      |
| 5,675,405 | A | * | 10/1997 | Schildmeyer | ........ G01N 15/065 |
|           |   |   |         |       | 356/339      |
| 6,498,641 | B1 | * | 12/2002 | Schildmeyer | ........ G01N 15/065 |
|           |   |   |         |       | 356/335      |
| 6,712,881 | B2 |   | 3/2004  | Hering et al. |     |
| 7,719,683 | B2 | * | 5/2010  | Ahn | ..................... G01N 15/065 |
|           |   |   |         |       | 356/337      |
| 8,208,132 | B2 | * | 6/2012  | Huetter | ................ G01N 15/065 |
|           |   |   |         |       | 356/37       |
| 2013/0180321 | A1 |   | 7/2013 | Shinohara et al. |  |
| 2013/0180325 | A1 |   | 7/2013 | Spandl et al. |     |

FOREIGN PATENT DOCUMENTS

| EP | 2012108 A2 | * | 1/2009 |
|----|------------|---|--------|
| EP | 2194370    |   | 6/2010 |
| EP | 2194371    |   | 6/2010 |
| WO | WO99/02957 | * | 1/1999 |

OTHER PUBLICATIONS

English Abstract of EP 2194370.
English Abstract of EP 2194371.
TSI Brochure on Condensation Particle Counter Model 3786, 2007.

* cited by examiner

*Primary Examiner* — Daniel S Larkin
(74) *Attorney, Agent, or Firm* — Dykema Gossett PLLC

(57) ABSTRACT

A condensation particle counter comprising a saturation unit (1) and a downstream condensation unit (2), through which at least one channel (5) for an aerosol flow passes between an inlet (3) and an outlet (4) that leads to a counting unit (16). The saturation unit (1) and the condensation unit (2) comprise a shell sleeve (12) having an inner shell wall (21) that is penetrated by a core (6), the core wall (20) and the inner shell wall (21) delimiting a channel (5) formed therebetween.

21 Claims, 4 Drawing Sheets

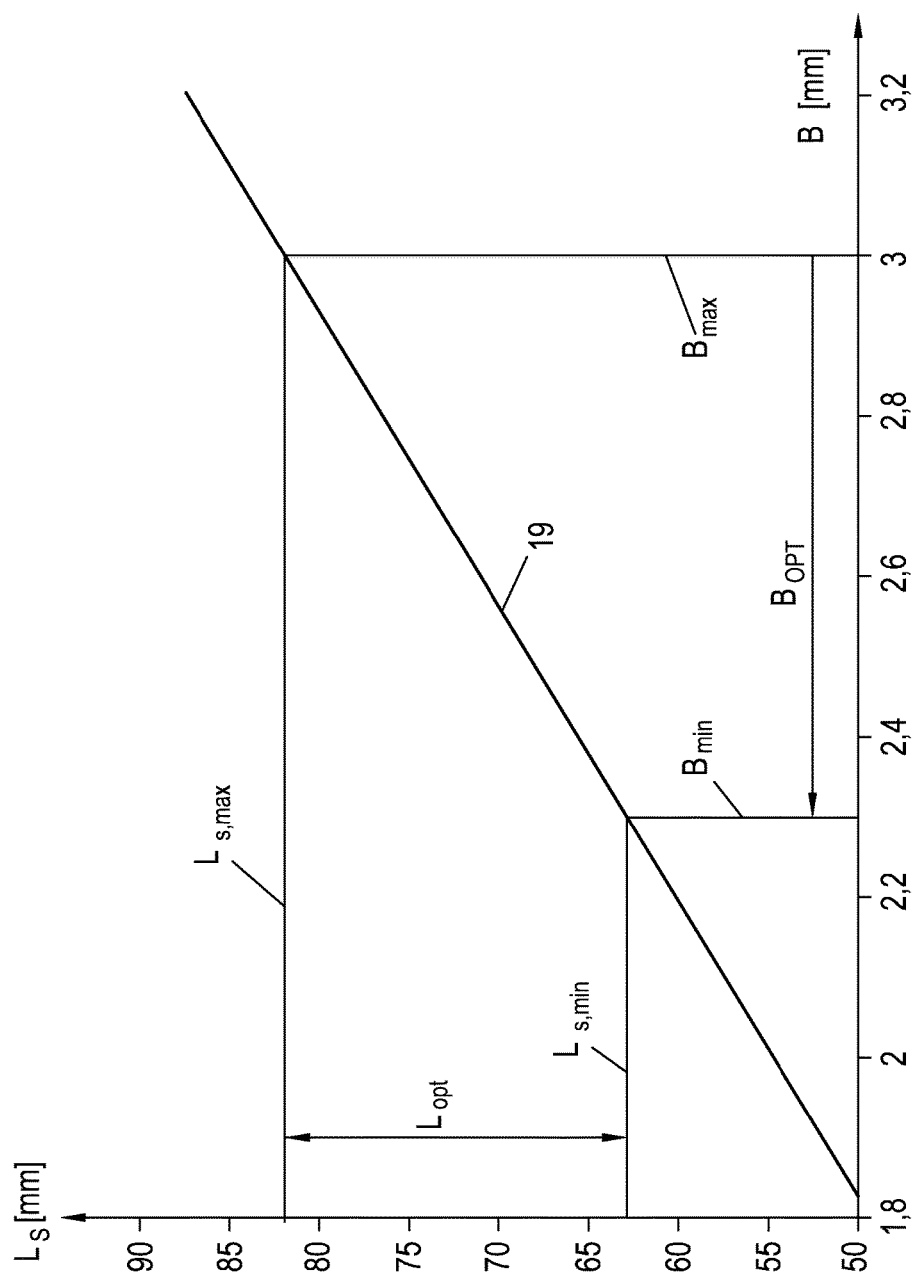

ated

Figure 1:
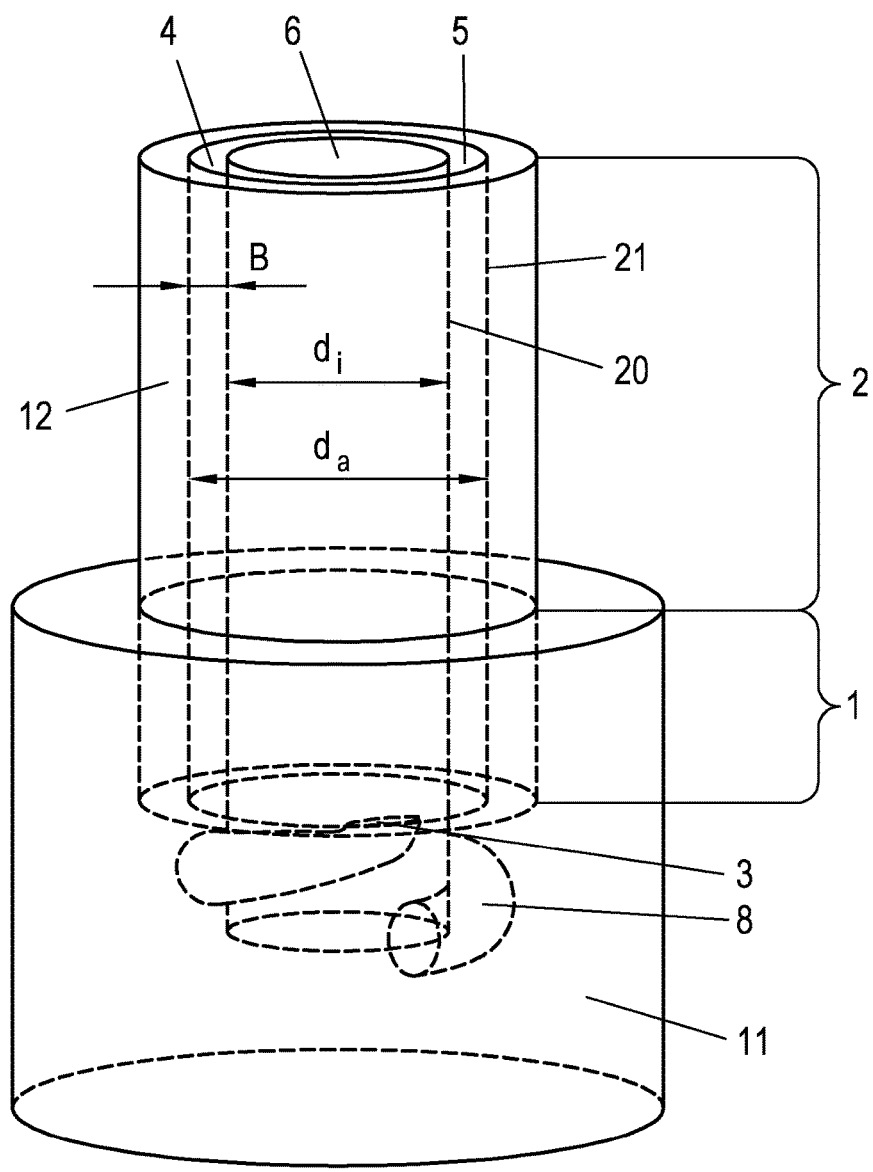

CONDENSATION PARTICLE COUNTER WITH SATURATION UNIT AND DOWNSTREAM CONDENSATION UNIT

BACKGROUND OF THE INVENTION

Field of the Invention

The invention relates to a condensation particle counter which includes a saturation unit and a downstream condensation unit, and through which at least one channel for an aerosol flow passes between an inlet and an outlet that leads to a counting unit.

The Prior Art

Condensation particle counters have long been known in the prior art, and are used, for example, in clean-room technology or to measure exhaust gas flows.

One example of the basic structure of a condensation particle counter can be found, for instance, in patent document EP 2194370 A1 or EP 2194371 A1. These patent documents disclose a condensation particle counter comprising a saturation unit, a condenser, and an optical measuring cell, the saturation unit being arranged so as to be inclined at an angle of about 6 to 7° and ascend in the direction of flow. It is composed of an elongated, square-shaped aluminum block, which is equipped with an electric heating device. The cylindrical inner wall of the aluminum block is lined with a porous coating made of foamed polyethylene, which is fed with a vaporizing working medium, e.g. butanol, via a reservoir. The aerosol flows from an inlet at the lower end of the saturation unit through same, a saturated atmosphere being generated therein, and arrives at the upper end of the saturation unit via a discharge opening into a vertically arranged and cooled riser tube which acts as a condenser and in which the supersaturated steam condenses on the particles. The particles, having been enlarged in this manner to a size of several micrometers in the condenser, then pass through a separation nozzle into a measuring chamber, in which the particles are detected and counted with the aid of a laser optical system. The particle flow is generated then by a vacuum pump that is connected downstream of the measuring chamber.

A manner of homogenizing the flow in the saturation unit that is further known from the above-mentioned publications is to arrange a displacement element, configured in the form of a rod, centrally in the flow channel. However, the L-shaped transition between the saturation unit and the condenser causes there to be flow disturbances in the condenser, and these lead to substantial particle losses and consequently incorrect measurement results. In addition, the currents result in a strongly contaminated counting efficiency curve in terms of the size of the aerosols needing to be grown.

There is generally a problem in the design of condensation particle counters in that the minimum overall length of the saturation unit required for the necessary saturation also entails limitations to the miniaturization of the device. The structure must also ensure that any particle losses are minimized. Particle losses can occur in particular if the flow channel in the saturation unit is too wide. A narrowing of the flow channel, however, means that the length of the saturation unit has to be increased.

With regard to the dimensions of the saturation unit and the condensation unit, the following standard values have been determined, for example, for a simple cylindrical channel through simulation of a volume flow of 1,000 sccm:

1.) Saturation unit
$L_s = 1167/R_s$
$R_s$ . . . Radius of the flow channel in the saturation unit [mm]
$L_s$ . . . Active saturator length [mm]
A diameter D=6 mm results in a constructional length of the saturation unit of at least 300 mm (representing about 77% of the value according to the above formula).

2.) Condensation unit
$L_k = 1390/R_k$
$R_k$ . . . Radius of the flow channel of the condensation unit [mm]
$L_k$ . . . cooled condenser length [mm]
A diameter D=10 mm results in a constructional length of the condensation unit of at least 200 mm (representing about 72% of the value according to the above formula).

The entire flow channel thus results in a minimum overall length of about 500 mm.

U.S. Pat. No. 3,738,751 discloses a discontinuously working condensation nucleus counter having a cylindrical saturation unit that is penetrated by a hollow core, wherein a coat lining is provided as a wicking element for the working fluid, the coat lining being arranged both on the outer wall of the cylinder and on the outer wall of the core. For the purpose of measurement, the atmosphere that has been saturated with the working fluid is suctioned through a line from the saturation unit and into a condensation chamber located in the hollow core of the saturation unit. Then, the pressure in the condensation chamber is reduced by a piston unit, thus forming the condensation on the particles. The particle fraction is then evaluated by means of an electro-optical measuring arrangement based on radioscopy of the condensation chamber.

The teachings from U.S. Pat. No. 3,738,751 cannot be readily shifted to continuously operating particle counters. In particular, the condenser in U.S. Pat. No. 3,738,751 is located centrally in the heated saturation unit, hindering the cooling of the condenser that is required for continuously operating devices. It is also suitable for the particle flow in the condenser to run upward from below, against the force of gravity, because so doing ensures that any condensate runs down the walls and thus does not contaminate the optical counting unit located downstream.

U.S. Patent Application Publication 2013/010180321 A1 discloses a particle counter in which the saturation unit comprises a shell sleeve, within which a substantially cylindrical and porous element is arranged as a saturation element. The porous element is penetrated by a core, wherein two vertical flow passages for the particle flow that run parallel to the core axis are arranged in the porous element in the region between the core and the shell sleeve. At least one gap is prevented between the porous element and the shell wall, in order to avoid an adverse capillary effect.

The invention addresses, inter alia, the problem of providing a condensation particle counter that combines a particularly compact design with enhanced performance.

SUMMARY OF THE INVENTION

This and other objects are achieved by a condensation particle counter of the kind mentioned at the beginning, in which the saturation unit and the condensation unit comprise a shell sleeve having an inner shell wall that is penetrated by a core, wherein the core wall and the inner shell wall delimit the channel formed therebetween. This embodiment allows a simple and cost-effective design that is combined with an advantageous flow pattern. The continuous particle flow passes through the saturation unit and the condensation unit from the inlet to the outlet, wherein a well-defined flow pattern having a preferably substantially laminar flow can be achieved over the entire channel. The mantel and core walls can then be spaced apart over the respective entire circumferences thereof so as to form the channel; however, the channel may also be configured in only one or more circumferential regions, with the mantel and core walls then being in contact with one another in the other regions.

The advantages according to the invention can thus be realized in a constructionally simple manner. In order to advantageously influence the flow pattern, the core wall and/or the shell wall may be formed so as to be smooth or contoured. For example, they may have a spiral contour.

Advantageously, the channel may have an annular cross-section with a core diameter $d_i$ and a she wall diameter $d_a$. The respective diameters may vary over the longitudinal extension of the channel. In one variant of the invention, the annular cross-section of the channel is constant along the longitudinal direction of the channel. This enables homogeneous supersaturation in the condensation unit with a short construction, wherein the core wall and the shell wall are preferably arranged concentrically. Alternatively, the core and/or shell walls could have, for example, a conical shape or the shape of a truncated cone.

In an advantageous embodiment of the invention, the channel is arranged so as to be substantially vertical when the condensation particle counter is used as intended. This ensures the flow of the condensate in the condenser and allows the reservoir to be arranged advantageously with respect to the saturation element(s).

Also advantageously, a condensate trap may be provided between the saturation unit the condensation unit, in order to collect the condensate flowing back in the condensation unit or in the direction of the saturation unit.

Advantageously, the condensate trap may be designed as a filtration element, e.g., in the form of a molecular sieve. This enables reuse of the returning condensate in the saturation unit, ensuring that the purity of the condensate corresponds to that of the equipment.

In another advantageous embodiment according to the invention, the channel runs in a straight line. A straight-line course without bends, curves, or edges makes it easier to assemble the unit.

In an exemplary and specific embodiment of the invention, the channel may have a gap width B in the range of about 2.3 to about 3.0 mm and a length $L_s$ of the saturation unit in the range of about 62 to about 82 mm. In the range of these dimensions, particle losses can be expected to be minimized. As compared to a saturation unit without a core and with a radius of 2.3 to 3.0 mm, this corresponds to a shortening of the required overall length by more than 70%.

Advantageously, a saturation element that can be impregnated with a working medium may be provided on the core wall and on the shell wall. The saturation element thereby covers the core and shell walls at least partially, or even completely. Arranging a saturation element on the core, as well, makes it possible to reduce the overall length of the saturation unit. Alternatively, it is also possible to use a simple metal section as a core, in order to realize a simple and inexpensive solution. Possible examples that can be used as the saturation element include a flat wicking element or wick, an open-pore foam material, or another material that is known in the prior art and is suitable for this purpose.

In an advantageous embodiment of the invention, the inner surface of the base body and/or the shell wall and/or the core wall may be coated, in the region of the surface of contact with the respective saturation element, with a material that lowers the interfacial tension between the working fluid and the surface adjoining the saturation element. This avoids disturbances from capillary effects at the interfaces.

Another advantageous embodiment of the invention provides that the core comprises cooling channels at least in the region of the condensation unit. This improves the condensation and thus once again reduces the length of the design.

Also advantageously, a conditioning unit for the aerosol flow may be provided between the outlet of the condensation unit and the counting unit. In one variant of the invention, a separation nozzle is provided between the outlet of the condensation unit and the counting unit, preferably downstream of a conditioning unit for the aerosol flow. This makes it possible to adapt the device to diverse counting units and to different operating conditions, and to continuously ensure a defined and substantially laminar flow.

According to another advantageous embodiment, a helical supply line may be placed upstream of the inlet to the saturation unit. This makes it possible to achieve a homogeneous flow with a low overall height, which in turn minimizes the particle losses. It is convenient for the core to be at least partially surrounded by the helical supply line.

The present invention shall now be described in greater detail, with reference to FIGS. 1 to 4, which, by way of example, illustrate advantageous embodiments of the invention in a schematic and non-restrictive manner.

BRIEF DESCRIPTION OF THE DRAWINGS

FIG. 1 illustrates the saturation unit and the subsequent condensation unit in a perspective, schematic view;

FIG. 2 illustrates a vertical sectional view of the unit in FIG. 1;

FIG. 3 illustrates a vertical sectional view of units downstream from the condensation unit; and FIG. 4 illustrates a diagram for explaining the relationship between height and gap width in the saturation unit.

DETAILED DESCRIPTION OF THE INVENTION

FIG. 1 illustrates a schematic view of the saturation unit 1 and the condensation unit 2 of the condensation particle counter according to the invention. The assembly comprises a base 11 in which a shell sleeve 12 comprising a core 6 arranged concentrically therein are arranged, wherein the surface of the shell sleeve 12 that faces the core 6 is designated a shell wall 21. The surface of the core 6 that faces the shell sleeve 12 is correspondingly designated a core wall 20.

The shell sleeve 12 and the core 6 protrude upward from the base 11. The shell sleeve 12 and the core 6 are spaced apart from one another so as to form a channel 5 having an annular cross-section, the inner diameter of the shell sleeve 12 corresponding to the outer diameter of the channel (shell diameter $d_a$) and the inner diameter of the channel corresponding to the core diameter $d_i$. $B=(d_a-d_i)/2$ thus applies for the gap width B between the shell wall 21 and the core wall 20. The gap width B is constant along the longitudinal extension of the channel 5 in the depicted embodiment, but can also vary.

A supply line 8 is provided in the base 11 and the aerosol flow intended to be analyzed is introduced via the supply line 8. The supply line 8 is guided substantially helically around the core and joins the lower end of the saturation unit 1 with an inlet 3 in the channel 5. The spiral or helical curvature of the supply line 8 defines the flow behavior of the aerosol flow within the channel 5, wherein preferably a substantially laminar flow is generated in the channel 5, the flow extending upward helically around the core and exiting at the outlet 4, after having flowed through the saturation unit 1 and the condensation unit 2. Preferably, the cross-section of the supply line at the inlet 3 is fitted to the annular cross-section in order to largely avoid flow edges. Depending on the requirements, another form may also be selected for the supply line 8, it being also possible to cause, for example, a laminar flow that is parallel to the core axis, or a turbulent flow.

Figure 2:
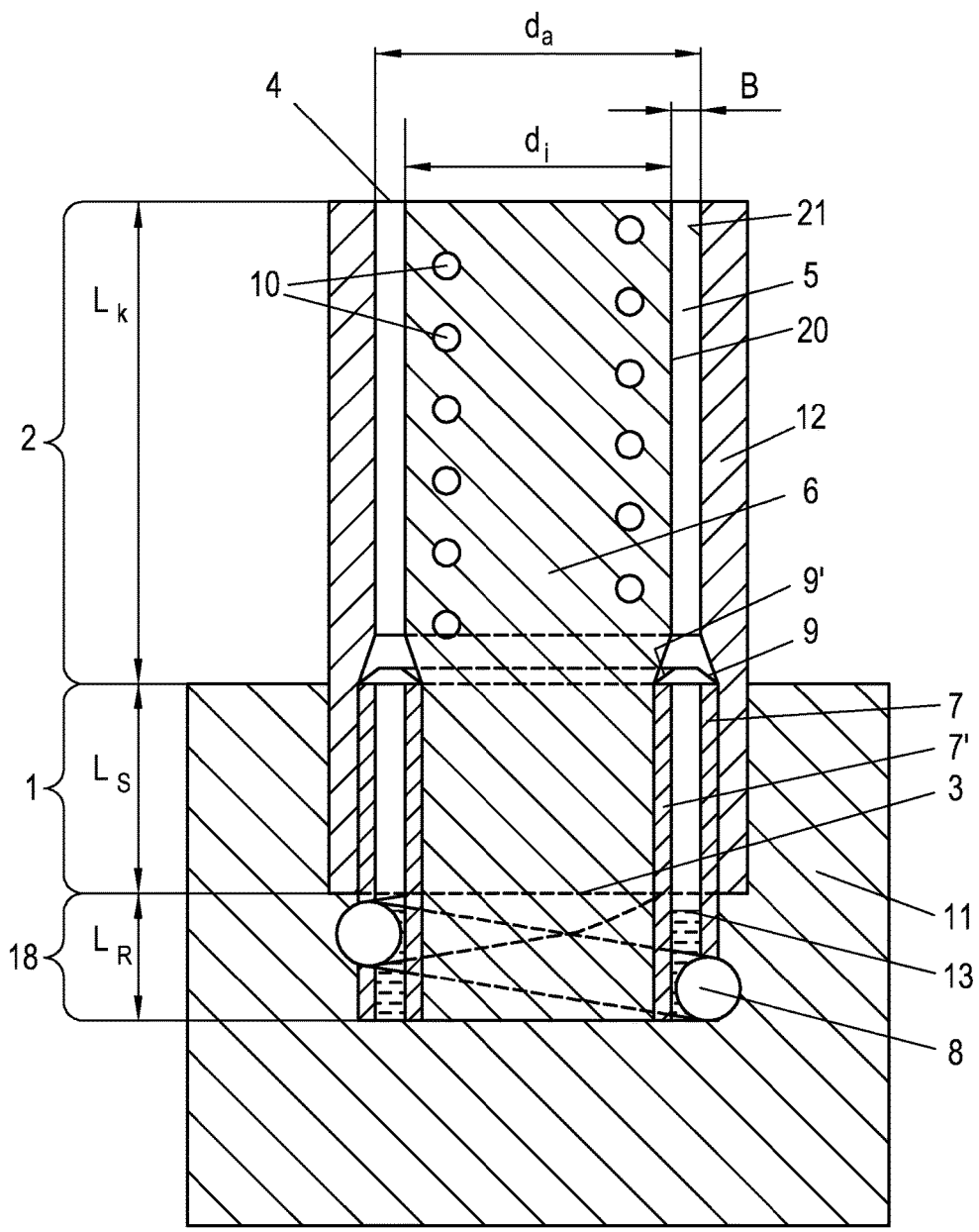

FIG. 2 illustrates the assembly illustrated in FIG. 1, again in a sectional view. Provided below the saturation unit 1 is a reservoir 18 for the working fluid 13, in the region where the helical supply line 8 also extends. Provided around the core 6 and at the shell wall 21 or in the region of the reservoir 18 on an inner wall of the base 11 are respective saturation elements 7, 7' which each extend over the total length $L_s$ of saturation unit 1 and downward into the reservoir 18, and at least partially cover the shell wall 21 and the core wall 20. In order to avoid disturbances from capillary effects, the inner surface of the base body 11 and/or the outer surface of the core 6 may be coated in the region of the surface of contact with the respective saturation elements 7, 7' with a material that lowers the interfacial tension between the working fluid and the surface adjoining the saturation elements 7, 7', so as to prevent a capillary effect. Possible examples that can be used as the coating material include Teflon® (The Chemours Company FC, LLC) or non-polar plastics. The lower ends of the saturation elements 7, 7' are immersed in the working fluid, e.g., butanol, and suck in the fluid like a sponge. The saturation unit 1 is heated by a heating device (not shown) provided in the base 11 in order to vaporize the working fluid 13 through the saturation elements 7, 7', so that a saturated atmosphere predominates at the upper end of the saturation device 1.

At the transition from the saturation unit 1 (which is arranged substantially within the base 11) to the condensation unit 2 projecting upwardly from the base 11, an annular condensate trap 9, 9' for the condensate flowing back on the walls of the condensation unit is arranged around the core 6 and on the shell wall 21, respectively. The condensate traps 9, 9' may be designed as microfilters/molecular sieves, so that the returning condensate is collected by the condensate traps 9, 9', is filtered therein, and thus recycled and delivered to the saturation elements 7, 7'. Alternatively, the condensate may also be discharged via a discharge line (not shown) and fed back to the reservoir after having been treated.

The transition from the saturation unit 1 to the condensation unit 2 happens substantially unhindered by the aerosol flow, wherein the flow extends helically further upward and is cooled in the condenser 2. The cooling takes place substantially by convention via the relatively thin shell sleeve 12. In order to enhance the cooling effect, cooling channels 10 through which a cooling medium flows may be provided in addition in the core. The shell sleeve 12 may also be actively cooled, for example via corresponding cooling channels or via cooling coils or cooling fins on the outer surface of the shell sleeve 12.

Figure 3:
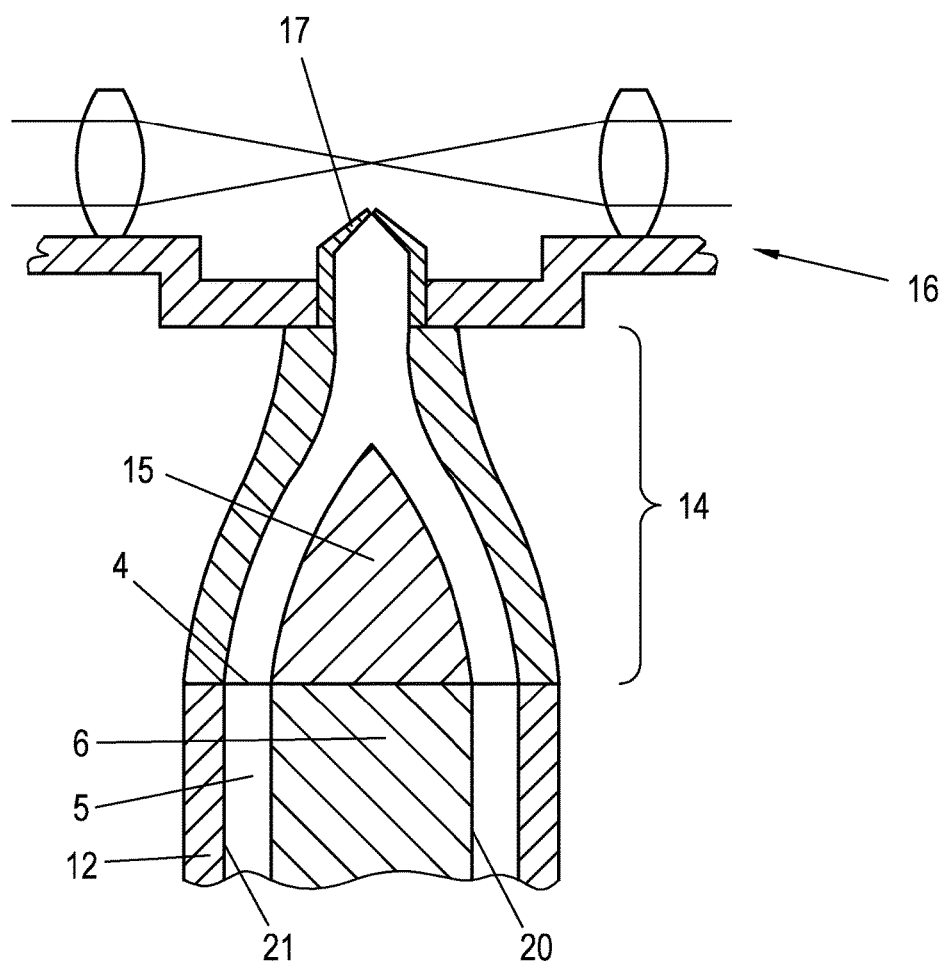

While the aerosol is flowing through the condensation unit 2, the working fluid condenses on the particles, which act as condensation nuclei and, en route to the condensation unit 2, grow because of this to a size that can be measured with an optical measuring device. For this purpose, the aerosol flow including the particles having received condensation are passed on to a counting unit after the outlet 4, wherein the flow cross-section after the outlet 4 may be adapted to the respective circumstances and needs. For this purpose, it is possible, as is schematically illustrated in FIG. 3, for example, for a conditioning unit 14 after the outlet 4 to join the annular flow cross-section back to a single continuous cross-section, wherein in FIG. 3, a sharply converging core extension 15 is subsequently provided to the core 6 in order to advantageously influence the flow. After the conditioning unit 14, the aerosol flow is fed to the counting unit 16, wherein the counting unit 16 in the instances depicted comprises a separation nozzle 17 by means of which the particles having received condensation are separated in order to be detected and passed through the focus of a laser optical device.

The conditioning unit 14 may also be provided with a cooling system in order to further condense the aerosol flow and further grow the particles in the conditioning unit 14. In such a case, the conditioning unit 14 could also be regarded as another condenser, wherein a two-stage condensation is realized.

FIG. 4 illustrates a diagram of the relationship between the gap width B and the length $L_s$ of the saturation unit, in the manner that this relationship has been determined through simulation for an exemplary embodiment according to the invention. The straight line 19 corresponds to an example for the determined optimum ratio $L_s/B$ through which an optimal active saturator length $L_s$ can be assigned to each gap width B. Other constraints such as the design and flow conditions having been taken into account, it is possible to define, for the gap width B, a suitable range $B_{OPT}$ that lies between a minimum gap width $B_{min}$ and a maximum gap width $B_{max}$. A corresponding length range $L_{OPT}$ of $L_{s,min}$ to $L_{s,max}$ for the saturation unit can be assigned to this range between $B_{min}$ and $B_{max}$, via the line 19.

In addition to the length $L_S$ of the saturation unit and the gap width B, it is also possible to optimize the length $L_R$ of the reservoir, the length $L_K$ of the condenser, the core diameter $d_i$, and the shell diameter $d_a$, which are shown in FIG. 2, in accordance with the respective requirements and operating conditions. The implementation of such an optimization is within the scope of knowledge of a person skilled in the art.

The invention claimed is:

1. A condensation particle counter comprising a saturation unit and a downstream condensation unit, and through which at least one channel for an aerosol flow passes between an inlet of the saturation unit and an outlet of the condensation unit that leads to a counting unit, wherein the saturation unit and the condensation unit comprise a shell sleeve having an inner wall, wherein the shell sleeve is penetrated by a core defining an outer wall, the outer wall of the core and the inner wall of the shell sleeve delimiting an annular channel therebetween, and including a condensate trap between the saturation unit and the condensation unit.

2. The condensation particle counter according to claim 1, wherein a cross-section of the annular channel is constant along a longitudinal direction of the channel.

3. The condensation particle counter according to claim 1, including a base body, and wherein the saturation unit is located within the base body and the condensation unit is vertically above the saturation unit.

4. The condensation particle counter according to claim 3, wherein at least one of an inner surface of the base body, the inner wall of the shell sleeve and the outer wall of the core is coated, in the region of a surface of contact with the respective saturation element, with a material that lowers interfacial tension between a working fluid and the surface adjoining the saturation element.

5. The condensation particle counter according to claim 1, wherein the condensate trap comprises a filtration element.

6. The condensation particle counter according to claim 1, wherein the annular channel extends in a straight line.

7. The condensation particle counter according to claim 1, wherein the annular channel has a gap width in a range of about 2.3 to about 3.0 mm and a length in a range of about 62 to about 82 mm.

8. The condensation particle counter according to claim 1, including a separation nozzle between the outlet of the condensation unit and the counting unit for the aerosol flow.

9. A condensation particle counter comprising a saturation unit and a downstream, condensation unit, and through which at least one channel for an aerosol flow masses between an inlet of the saturation unit and an outlet of the condensation unit that leads to a counting unit, wherein the saturation unit and the condensation unit comprise a shell sleeve having an inner wall that is penetrated by a core defining an outer wall, the outer wall of the core and the inner wall of the shell sleeve delimiting an annular channel therebetween, and including a saturation element impregnated with a working medium on the outer wall of the core and on the inner wall of the shell sleeve.

10. The condensation particle counter of claim 9, wherein a cross-section of the annular channel is constant along a longitudinal direction of the channel.

11. The condensation particle counter of claim 9, including a base body, and wherein the saturation unit is located within the base body and the condensation unit is vertically above the saturation unit.

12. The condensation particle counter of claim 11, wherein at least one of an inner surface of the base body, the inner wall of the shell sleeve and the outer wall of the core is coated, in the region of a surface of contact with the respective saturation element, with a material that lowers interfacial tension between a working fluid and the surface adjoining the saturation element.

13. The condensation particle counter of claim 9, including a condensate trap between the saturation unit and the condensation unit.

14. The condensation particle counter of claim 9, wherein the annular channel extends in a straight line.

15. The condensation particle counter of claim 9, wherein the annular channel has a gap width in a range of about 2.3 to about 3.0 mm and a length in a range of about 62 to about 82 mm.

16. The condensation particle counter of claim 9, including a separation nozzle between the outlet of the condensation unit and the counting unit for the aerosol flow.

17. A condensation particle counter comprising a saturation unit and a downstream condensation unit, and through which at least one channel for an aerosol flow passes between an inlet of the saturation unit and an outlet of the condensation unit that leads to a counting unit, wherein the saturation unit and the condensation unit comprise a shell sleeve having an inner wall that is penetrated by a core defining an outer wall, the outer wall of the core and the inner wall of the shell sleeve delimiting an annular channel therebetween, and wherein the core comprises cooling channels.

18. A condensation particle counter comprising a saturation unit and a tion unit and the condensation unit comprise a shell sleeve having an inner wall that is penetrated by a core defining an outer wall, the outer wall of the core and the inner wall of the shell sleeve delimiting an annular channel therebetween, and including a conditioning unit for the aerosol flow between the outlet of the condensation unit and the counting unit.

19. A condensation particle counter comprising a saturation unit and a downstream condensation unit, and through which at least one channel for an aerosol flow passes between an inlet of the saturation unit and an outlet of the condensation unit that leads to a counting unit, wherein the saturation unit and the condensation unit comprise a shell sleeve having an inner wall that is penetrated by a core defining an outer wall, the outer wall of the core and the inner wall of the shell sleeve delimiting an annular channel therebetween, and including a helical supply line upstream of the inlet of the saturation unit.

20. The condensation particle counter according to claim 19, wherein the core is surrounded at least partially by the helical supply line.

21. A condensation particle counter which comprises:
a shell sleeve and a core which extends within the shell sleeve to define an annular channel between the shell sleeve and the core, a portion of one end of the shell sleeve with core therein defining a saturation unit and a portion of an opposite end of the shell sleeve with core therein defining a condensation unit, and a saturation element impregnated with a working medium on an outer wall of the core and on an inner wall of the shell sleeve, and
a counting unit,
wherein aerosol entering the annular channel at an inlet of said saturation unit flows through the annular channel and exits at an outlet of the condensation unit and flows to the counting unit.

\* \* \* \* \*